(12) United States Patent
Tyvoll et al.

(10) Patent No.: US 7,534,618 B2
(45) Date of Patent: May 19, 2009

(54) SYSTEMS AND METHODS FOR MEASURING GLYCATED HEMOGLOBIN

(75) Inventors: David A. Tyvoll, San Diego, CA (US); Kirk W. Norton, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 11/881,531

(22) Filed: Jul. 27, 2007

(65) Prior Publication Data
US 2007/0267361 A1 Nov. 22, 2007

Related U.S. Application Data

(63) Continuation-in-part of application No. 11/261,741, filed on Oct. 28, 2005.

(51) Int. Cl.
*G01N 1/28* (2006.01)
(52) U.S. Cl. .......................... 436/67; 436/45; 436/177; 422/72
(58) Field of Classification Search .................. 436/67, 436/45, 177; 422/99, 72
See application file for complete search history.

(56) References Cited

U.S. PATENT DOCUMENTS

| | | | |
|---|---|---|---|
| 5,284,773 A * | 2/1994 | Kulkarni et al. .............. 436/52 |
| 5,550,060 A * | 8/1996 | Saunders et al. .............. 436/63 |
| 5,837,546 A | 11/1998 | Allen et al. | |
| 5,932,480 A | 8/1999 | Maruo et al. | |
| 5,968,839 A | 10/1999 | Blatt et al. | |
| 6,174,734 B1 | 1/2001 | Ito et al. | |
| 6,316,265 B1 | 11/2001 | Lee et al. | |
| 6,399,293 B1 | 6/2002 | Pachl et al. | |
| 6,582,964 B1 | 6/2003 | Samsoondar et al. | |
| 6,818,416 B2 | 11/2004 | Pachl et al. | |
| 6,946,100 B2 * | 9/2005 | Yokoi et al. ................... 422/58 |
| 2007/0099301 A1 * | 5/2007 | Tyvoll et al. .................. 436/67 |

FOREIGN PATENT DOCUMENTS

WO WO98/53311 11/1998

OTHER PUBLICATIONS

Jayadev, Suprya, Percoll Gradient, Aug. 27, 1991, http://www.musc.edu/BCMB/ceramide/protocols/0016.html.*

Gifford, Sean C., "Parallel Microchannel-Based Measurements of Individual Erythrocyte Areas and Volumes", Biophysical Journal, vol. 84, Jan. 2003, pp. 623-633.

Stivers, Carole R., "A Miniaturized Self-Contained Single-Use Disposable Quantitative Test for Hemoglobin Alc in Blood at the Point of Care", Diabetes Technology & Therapeutics, vol. 2, No. 4, 2000.

Professional-Use Product Insert for Alc Now, manufactured by Metrika, 90067 rev B.

Medical Devices Agency Evaluation Report, MDA 02098.

(Continued)

*Primary Examiner*—Jill Warden
*Assistant Examiner*—Rebecca Fritchman

(57) ABSTRACT

Systems and methods for fractionating components of a sample are disclosed herein. A method of fractionating components of a sample includes establishing a solution density gradient in a capillary channel, applying the sample to the capillary channel, and centrifuging the sample in the capillary channel, thereby separating the components of the sample by density.

16 Claims, 7 Drawing Sheets

OTHER PUBLICATIONS

Dale, George L. et al., "Density Fractionation of Erythrocytes by Percoll/Hypaque Results in Only a Slight Enrichment for Aged Cells", *Biochimica et Biophysica Acta*, 1036 (1990) pp. 183-187.

Steigert, J. et al., "Integrated Sample Preparation, Reaction, and Detection on a High-Frequency Centrifugal Microfluidic Platform", *Technology Review*, 2005, 11 pages.

* cited by examiner

SYSTEMS AND METHODS FOR MEASURING GLYCATED HEMOGLOBIN

CROSS-REFERENCE TO RELATED APPLICATIONS

The present application is a continuation-in-part of copending U.S. patent application Ser. No. 11/261,741, titled SYSTEMS AND METHODS FOR MEASURING GLYCATED HEMOGLOBIN, filed Oct. 28, 2005, and hereby incorporated by reference.

BACKGROUND

Red blood cells (RBC), or erythrocytes, are responsible for the transport of oxygen throughout the body. Specifically, hemoglobin, which is part of a healthy red blood cell, is an iron-containing respiratory macromolecule which functions in its oxygenated form to carry oxygen from the lungs to tissue sites. As is known, red blood cells have a membrane that is freely permeable to glucose. When glucose or other sugar moieties enters a red blood cell, glycated hemoglobin (GHb) can be formed. Glycated hemoglobin refers to various hemoglobin derivatives formed by covalent attachment of sugar moieties, in particular glucose. The amount of glycated hemoglobin formed is related to glucose concentration in the blood, as well as to the duration of exposure to glucose. The common index of glycated hemoglobin is known as $HbA_{1c}$, and the ratio of $HbA_{1c}$ to total hemoglobin is known as % $HbA_{1c}$.

As a general matter, red blood cells have a lifetime of approximately 120 days, and the amount of glycation of hemoglobin varies as a function of the 120 day lifetime of the cell. As the reaction of glucose with hemoglobin molecules is slow and generally irreversible in vivo, the amount of glycated hemoglobin ($HbA_{1c}$) has traditionally been considered to be an accurate index of blood glucose concentrations over the previous 3-4 months. Accordingly, diabetes patients are advised to check their $HbA_{1c}$ value every 3-4 months. For example, the American Diabetes Association (ADA) recommends an $HbA_{1c}$ test about 2 to 4 times per year and further recommends an $HbA_{1c}$ level below 7%.

The determination of total hemoglobin can be performed by simple absorbance or reflectance measurements. Typically the iron is reduced by potassium ferricyanide to create methemoglobin, which is measured at 565 nm. The determination of the amount of glycated hemoglobin can be performed by numerous methods known in the art such as by competitive or immunometric assays. In the latter, the antigens can be insolubilized on a solid phase and a labeled antibody is incubated in their presence. The antibody-antigen complex can be detected by optical or fluorescent methods. This method can be practiced on about 10 μl of blood. However, this method is carried out using a random cell sample collected from the blood, and thus, provides a single datum of average glucose regulation history at a specific point in time. The measured average value can be skewed toward newer cells because they are more prevalent. Yet the measured average amount of glycation of hemoglobin is often understated for younger cells because of their brief exposure to glucose, when compared to older cells. Because of this, testing glycated hemoglobin every 3-4 months will not accurately reflect the quality of glucose regulation in some diabetic patients. For instance, a diabetic patient can be systematically under-regulating their glucose levels for 1-3 months, and then over-regulating their glucose levels during the most recent 30 days prior to the test. Because of the large influence that the newest red blood cells have on $HbA_{1c}$ testing, the average glycated hemoglobin can appear in the normal range, thus misleading the patient and the caregiver as to the quality of glucose regulation. As a result, it would be beneficial to provide a practitioner or a subject more detailed information related to patient glucose levels over shorter periods of time, as well as provide more accurate information related to compliance with respect to glucose regulation.

BRIEF DESCRIPTION OF THE DRAWINGS

Features and advantages of embodiments of the present disclosure will become apparent by reference to the following detailed description and drawings. For the sake of brevity, reference numerals or features having a previously described function may not necessarily be described in connection with other drawings in which they appear.

DETAILED DESCRIPTION

Figure 1:
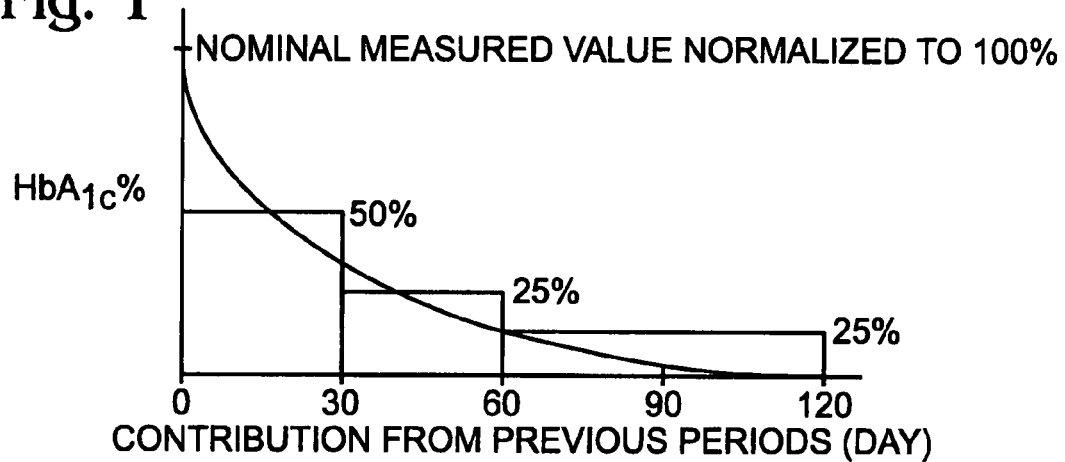
FIG. 1 is a graph depicting $HBA_{1c}$ levels as it generally relates to cell age.

It is to be understood that the embodiments disclosed herein are not limited to the particular process and materials discussed herein, and as such, may vary to some degree. It is also to be understood that the terminology used herein is for the purpose of describing particular embodiments, and is not intended to be limiting, as the scope of the present invention will be defined by the appended claims and equivalents thereof.

The following terminology will be used herein.

The singular forms "a," "an," and "the" include plural referents unless the context clearly dictates otherwise.

As used herein, the terms "microfluidic coupon" or "coupon" refer to a device used to centrifuge and/or manipulate one or more microfluids, generally for the purposes of testing the fluid or liquid in a centrifugation test regime. Suitable microfluidic coupons include, but are not limited to, disk-shaped devices formed of poly(methylmethacrylate) (PMMA), acetonitrile-butadiene-styrene (ABS), polycarbonate, etc. While not so limited, such disks can be similar in appearance to well-known optical disks, e.g., compact disks (CDs). It is also to be understood that such materials may optionally include coatings to minimize sticking and aggregation of cells. Coatings used herein can include, but are not limited to, polyethylene glycols (PEG), polysilicones and polydimethylsiloxanes (PDMS), and organic/silicone copolymers (PEG-silanes). Such coatings may also include detergents and surfactants, which may be present in amounts sufficient to prevent sticking and aggregation, but insufficient to cause cell lysis, except where desired.

As used herein, the term "valve" includes both passive valves and active valves. Active valves include valves having a mechanical valving gate of some type, e.g., paraffins or waxes, optically activated materials, heat-activated valves, mechanical valves, etc.; whereas passive valves are static valves with no moving parts that act as a fluid valve due primarily to its geometric configuration and/or size, e.g., microfluidic valves where fluid dynamics and/or force on fluid causes fluids to pass through microchannels, etc.

As used herein, the term "microfluidics" and "microfluid" are to be understood to refer to fluids manipulated in systems that confine the fluids within geometric channels, passages, reservoirs and other chambers having at least one dimension less than about 1 mm. Similarly, the terms "microfluidic channel," or "microchannel" are to be understood to refer to channels having at least one dimension less than about 1 mm.

As used herein, the term "centrifuge," and its related terms "centrifugation" and "centrifuged," are to be understood to refer to a process in which a liquid is subjected to centripetal forces induced by rotating a reservoir in which the liquid is stored. While the term centrifuge is generally used to refer to a process in which two or more constituents of a liquid are separated due to centripetal force, the use of the term herein is not limited to any particular degree of separation of constituents of the liquid. Thus, a liquid can be centrifuged even when it has not yet exhibited visible separation of liquid constituents.

When referring to "age-specific group(s)" of red blood cells, it is to be understood that not all cells with an age specific group must meet the age profile, as there will typically be cells within an age specific group that do not fit the age profile. This is due, at least in part, to the typically imprecise methods of separating cells by age. To the extent that perfect age segregation can be carried out, that type of separation certainly falls within the present definition. However, for practical purposes, a perfect segregation may not be possible. Thus, the term "age-specific group(s)" means that the group of red blood cells statistically includes more cells within a specific age group than a sample of red blood cells taken from a random sample.

When referring to fluids such as "liquids," it is to be understood that not all constituents of the liquid are necessarily in liquid form. For example, blood is considered to be a liquid, even though it has solid cell constituents suspended therein. It is to be further understood that the term "liquids" as used herein also includes those having all constituents in liquid form.

In accordance with an embodiment of the present disclosure, a method of measuring glycated hemoglobin includes the steps of: establishing multiple age-specific groups of red blood cells, and measuring $HbA_{1c}$ levels of at least one of said groups. In another embodiment, a system for measuring glycated hemoglobin includes a separating device configured to separate red blood cells into multiple age-specific groups, and a measuring device configured to measure $HbA_{1c}$ levels of at least one of these groups. In these embodiments, the % $HbA_{1c}$ can also be calculated by determining the total hemoglobin as well. Embodiments of the method and system disclosed herein provide an approach to solving a problem associated with measuring average glycated hemoglobin levels over a period of 3-4 months.

As can be seen in FIG. 1, about 50% of the $HbA_{1c}$ is provided by the red blood cells that are 30 days old or younger; about 25% of the $HbA_{1c}$ is provided by the red blood cells that are from 30 to 60 days old; and about 25% of the $HbA_{1c}$ is provided by the red blood cells that are from 60 to 120 days old. Thus, when measuring the $HbA_{1c}$ levels in a typical blood sample, a skewed picture of the overall $HbA_{1c}$ index is obtained.

Thus, in accordance with the present disclosure, it has been recognized that it would be desirable to obtain information about $HbA_{1c}$ levels that is red blood cell age specific, rather than to obtain information about average $HbA_{1c}$ levels over a period of months. In other words, in addition to learning of $HbA_{1c}$ values in relation to unglycated hemoglobin generally in blood sample, it would be more beneficial to know the $HbA_{1c}$ levels of a blood sample in relation to discrete age groups of red blood cells from unglycated hemoglobin, providing a more accurate picture of a blood sugar history of an individual. In one specific embodiment, it would also be beneficial to carry out this analysis using a small, portable device that could easily be used, and could be located in a home or a doctor's office. It would also be desirable if such a device could function using a minimal volume of blood, for instance less than 50 μl (approximately 1-2 drops). One or more of these desirable features can be achieved in accordance with various aspects of the present disclosure.

It has been recognized that separating cells based on a predetermined physical property before measuring $HbA_{1c}$ levels in blood can provide a more accurate picture regarding patient compliance over the entire life of red blood cells. In other words, as a sample of red blood cells includes both young and old blood cells, and as young blood cells contribute more extensively to $HbA_{1c}$ levels than older blood cells, by separating these cells along a gradient according to age of cells and subsequently conducting one or more $HbA_{1c}$ analyses, a more accurate and time sensitive picture of the $HbA_{1c}$ levels over a 3-4 month period can be obtained.

The segregation of red blood cells by age can be carried out using a number of techniques. One technique is counterflow centrifugation (elutriation), which separates particles of smaller diameter or size from those of larger diameter or size. For the case of red blood cells, it is known that the size dominates the balance between sedimentation and streaming. Thus, while older red blood cells are smaller and denser than young blood cells, they elute first during the centrifugation. Other techniques can rely on other chemical or physical indicators of cell age, including membrane protein ratios, and Theological properties. These latter factors may contribute to changes in the electronic properties of the cells. In particular, differences in electronic opacity (the ratio of radio frequency impedance to dc impedance) are also related to the red blood cell age. In light of this, the dielectric properties of the cells also correlate with their age, which means that the cells can be microscopically segregated based on their different dielectric properties. Other microscopic means, which may include the use of a microscope, to segregate the cells can rely on cell density and/or mechanical/rheological properties, such as elasticity and deformability. In particular, microchannel devices may be used to segregate a population of red blood cells based on their age. Thus, there are a number of ways of segregating red blood cells based upon their age. Such separations can be carried out in accordance with aspects of the present disclosure for the purpose of determining $HbA_{1c}$ levels based on cell age.

In addition, it is to be understood that precautions may be taken to minimize conditions that lead to cell stress, since this can reduce the efficiency of the segregation. These precautions include, but are not limited to, the use of anti-coagulants such as heparin or EDTA in a buffer, avoidance of excessive centripetal forces, avoidance of excessive temperature deviations, etc.

Figure 2:
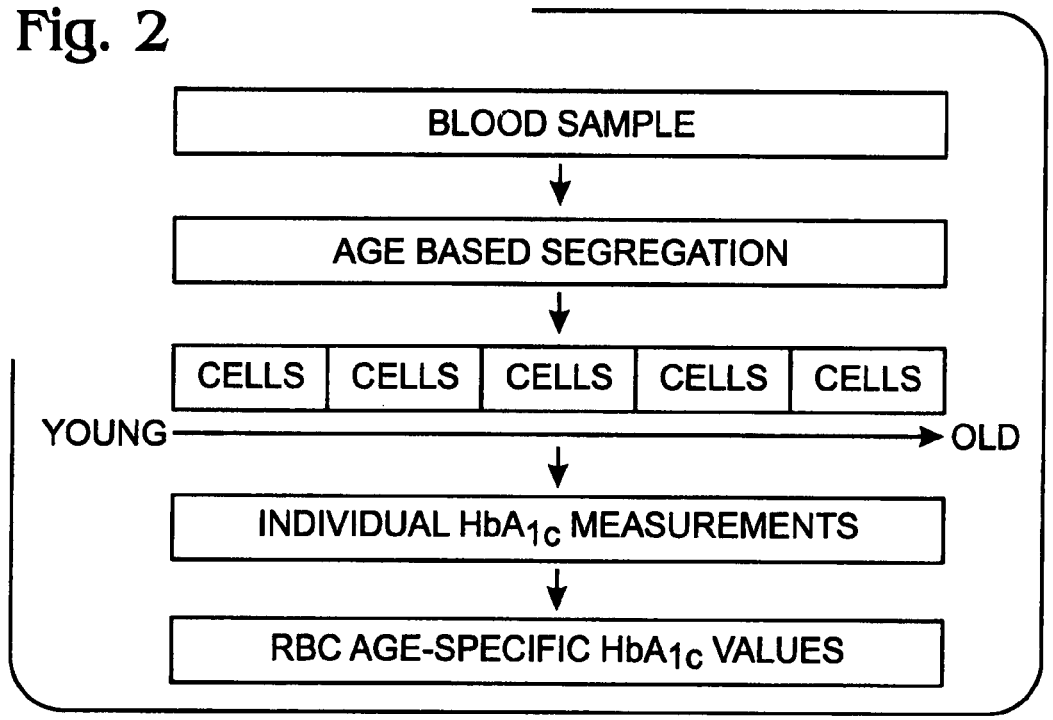
FIG. 2 is a flow diagram depicting an embodiment of a general approach to measuring $HBA_{1c}$ levels using age-based cell segregation.

A general scheme which illustrates a selected aspect of the present disclosure is shown in FIG. 2, where a blood sample is first separated based on age, e.g., a gradient from young to old or vice versa. The resulting cell gradient can be defined by grouping cells that are statistically likely to be close in age (based on one or more of size, density, dielectric response, etc.). Each group can then be evaluated individually for $HbA_{1c}$ levels. The number of groups can be as few as two groups (e.g., cells less than 1 to 3 months old compared to cells greater than 1 to 3 months old), to as many distinct groups as a practitioner deems appropriate (e.g., from 3 to 10 or more groups). Alternatively, one or more discrete group(s) at either end or in the middle of the age gradient can be evaluated.

It should be noted that the cell separation described herein need not necessarily result in a complete separation of groups of cells, as cells can be organized along a gradient. Further, it is notable that when using a physical cell property to approximate age, some cells may have an age that does not fit the statistical profile of the physical property used to organize the cells along the cell gradient. However, such markers tend to be accurate, and thus, anomalies where cell age does not fit the physical profile used to separate the cells becomes less significant. Further, even if such an age-based gradient is not completely accurate, as long as the gradient provides age-related cell organization that is more age-related than a random blood sample, the presently disclosed methods offer advantages for measuring $HbA_{1c}$ levels.

As previously described in U.S. Patent Publication No. US 2007/0099301 (incorporated herein by reference), the red blood cells of interest may be separated as a function of their size and/or density, for example using counterflow centrifugation. However, the use of density gradient centrifugation offers additional advantages for the separation of red blood cells. The present disclosure therefore provides systems and methods for fractionating components of a sample, including establishing a solution density gradient in a capillary channel, applying the sample to the capillary channel, centrifuging the sample in the capillary channel, and fractionating the components of the sample by density. The method may be used to measure $HbA_{1c}$ levels of age-specific groups of red blood cells.

Density gradient centrifugation may include rate zonal centrifugation or isopycnic centrifugation. Rate zonal centrifugation typically employs a solution gradient having a density less than that of the sample of interest. In this case, fractionation of the sample may be achieved by centrifuging the sample for a specific length of time. Alternatively, isopycnic centrifugation utilizes a solution gradient with a broad density range, typically broader than the density rage of the sample of interest. During isopycnic centrifugation, the cells will generally migrate to their isopycnic point, thus establishing a fractionation based on cell density at equilibrium.

The desired density gradient solution may be prepared from any appropriate combination of solvent and solute, provided that the resulting solution is compatible with the sample of interest. In one embodiment of the disclosed method, density gradient solutions for fractionating red blood cells may be conveniently prepared using a density gradient reagent, such as Iodixanol (OPTIPREP™) or Iohexol (OMNIPAQUE™), among others. Solutions of such density gradient reagents may have low osmolarity and an appropriate density for fractionating red blood cells.

The selected density gradient reagent may form a desired density gradient by any of a variety of convenient methods. For example, a solution of uniform solution density may be treated with one or more freeze-thaw cycles. In general, increasing the number of freeze-thaw cycles applied to the solution causes the gradient to be markedly less dense at the top. A gradient generated in this fashion may have an approximately linear density gradient. Alternatively, other, non-linear density profiles can also be generated. This freeze-thaw cycle method of gradient formation can generate density gradient profiles that are quite reproducible.

In the interest of both economy and efficiency, it may be desirable to utilize methods that require small volumes of solvent and/or small volumes of sample, such as methods utilizing a microfluidic device. A microfluidic device is a device that utilizes small volumes of fluid, for example as little as a few nanoliters of fluid. Microfluidic devices may use a variety of channels, reservoirs, chambers, and/or valves having various geometries to prepare, transport, and/or analyze samples. Microfluidic devices may rely upon a variety of forces to transport fluids through the device, including injection, pumping, applied suction, capillary action, osmotic action, thermal expansion and contraction, and centrifugation, among others. In one non-limiting example, a desirable microfluidic device is configured to be spun by a centrifuge, and centrifugal forces are utilized to transport the desired fluids through the microfluidic device as desired.

A microfluidic coupon may include a substrate that has been microfabricated to define the various desired channels, wells, and/or chambers for the analysis of interest. The channels and elements of the microfluidic coupon may be fabricated on the surface of the substrate, and then a cover may be adhered over the substrate surface. Typically, the cover is transparent, such that the transport of fluids throughout the microfluidic device can be determined via visual observation, or by optical detection and analysis.

Figure 3:
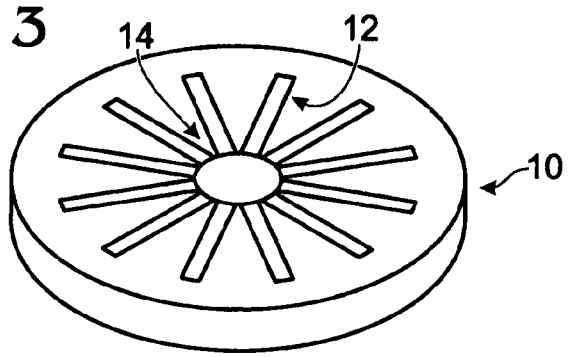
FIG. 3 is a schematic perspective view of an embodiment of a microfluidic coupon.

An exemplary microfluidic coupon 10 is depicted schematically in FIG. 3. Microfluidic coupon 10 is in the form of a disc, and includes a plurality of capillary channels 12 oriented in a radial pattern. The microfluidic coupon 10 is configured so that a density gradient can be established in one or more of the channels 12. The open ends of the channels 12

(the end toward the axis of rotation) may be sealed by one or more seals 14. In one aspect of the microfluidic coupon 10, as shown in FIG. 3, a single seal 14 covers the open end of each channel 12. Alternatively each channel 12 could be sealed by an individual cap or cover. Seal 14 may incorporate any of a number of sealing mechanisms, including a single-use or multiple-use plug or cap, or an adhesive cover. Seal 14 is generally removed immediately prior to the application of a sample of interest to channel 12.

The entrance of each capillary channel 12 can be an individual or shared reservoir. The reservoir may be configured to receive a pure blood sample or other red blood cell-containing sample, a buffered blood sample, or a non-blood sample such as a buffer fluid. Useful buffers for the disclosed methods may include phosphate buffered saline (PBS), derivatives of PBS, and other biologically compatible buffering agents.

Each capillary channel 12 is configured to facilitate the creation of a solution density gradient within the channel 12. In one aspect of the microfluidic coupon 10, the channel 12 is configured to establish a density gradient through the centrifugation of two or more individual solutions. In another aspect of the microfluidic coupon 10, the channel 12 is configured to establish a density gradient through one or more freeze-thaw cycles. However, it is to be understood that any method of establishing a solution density gradient in at least one channel 12 of the microfluidic coupon 10 is a suitable method for the purposes of the present disclosure.

Where the density gradient is established using two (or more) individual solutions having distinct densities, the solutions are typically kept separate until the formation of the gradient is desirable. For example, the two solutions may be present in the capillary channel 12, but they may be kept separated by use of a valve or a temporary barrier.

The barrier separating two distinct solutions may be a physical barrier that physically prevents the two solutions from mixing. Such a barrier should be readily removable without disturbing the ability of the capillary channel 12 to house a density gradient. For example, the barrier may take the form of a wax plug. The wax plug may physically separate the two or more solutions present in the capillary channel 12, but upon melting the wax plug, the solutions may then mix, enabling the formation of the desired density gradient. Where the barrier can be removed by heating, the barrier may be melted by resistive heating, optical heating, ultrasonic heating, or other means of heating.

Alternatively, the barrier may be a region of the capillary channel 12 where the walls of the channel 12 have been treated to repel the solutions in the capillary channel 12. For example, where each solution is an aqueous solution, the barrier region may be treated to render the walls of the channel 12 hydrophobic. This "liquid valve" may incorporate regions having a hydrophobicity that is matched to one or more of the capillary dimensions, centrifugation forces applied, and the surface tension of the fluid(s) in order to provide a valving mechanism. That is, in the absence of centrifugation, the two or more solutions remain separate, but upon centrifugation, the "upper" solution (toward the axis of rotation) may be forced through the hydrophobic region by the applied forces.

Figure 4:
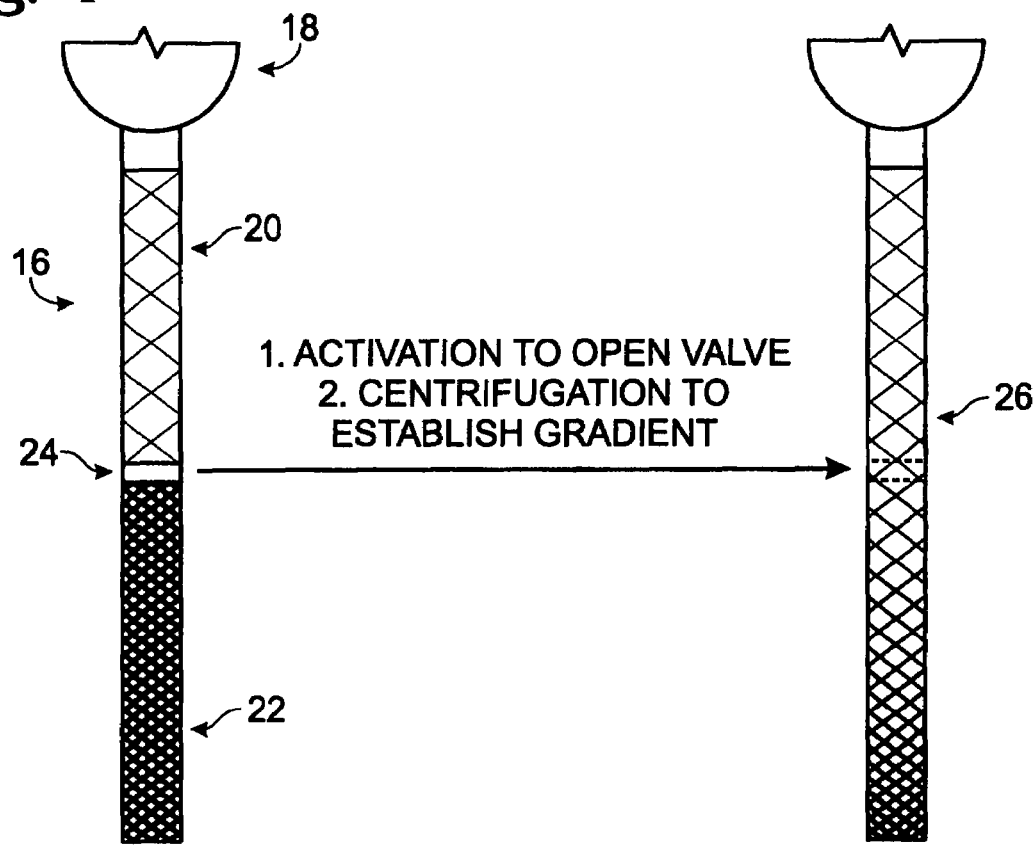
FIG. 4 is a schematic view of an embodiment of a capillary channel holding a first solution and a second solution separated by a barrier.

An exemplary capillary barrier 24 is depicted in FIG. 4. In capillary channel 16, equipped with seal 18, a first solution 20 having a first density is separated from a second solution 22 having a second density by a barrier 24, where the barrier is either a physical barrier, or a hydrophobic liquid valve. After activation to open barrier 24, either by heating, or by centrifugation, further centrifugation of the capillary channel 16 provides a solution 26 that exhibits a density gradient.

Although the desired gradient may also be established without centrifugation, this process takes considerably longer. As an internal control, one or more of the solutions used to prepare the density gradient may incorporate a density standard, or control. For example, colored beads having a known density may be present in the capillary channel 12, 16 prior to establishing the density gradient.

Figure 5:
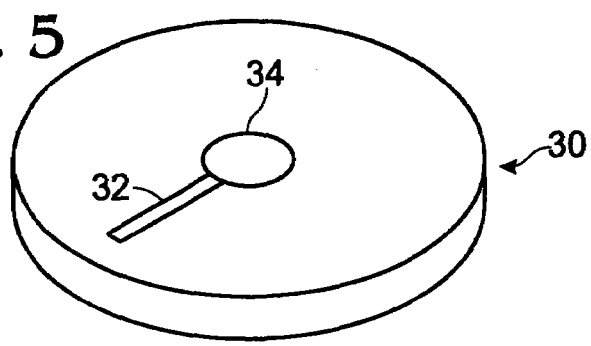
FIG. 5 is a schematic perspective view of another embodiment of a microfluidic coupon.

As an alternative to centrifugation, a density gradient may be established by subjecting a solution to one or more freeze-thaw cycles. While one cycle may be sufficient to achieve the desirable gradient, some embodiments require repeated freeze-thaw cycles to achieve the gradient. Regardless of the number of cycles use, it is to be understood that cycles should generally be controlled. Since the capillary channel 12, 16 is preferably substantially upright during the freeze-thaw cycles, the microfluidic coupon 10 will either have a limited number of capillary channels 12, 16, or a limited number of existing channels 12, 16 may be utilized. Additionally, since a single solution is typically used, the capillary channel 12, 16 need not include a barrier 24. An example of such a microfluidic coupon 30 is shown in FIG. 5, having a single capillary channel 32, and seal 34.

Figure 6:
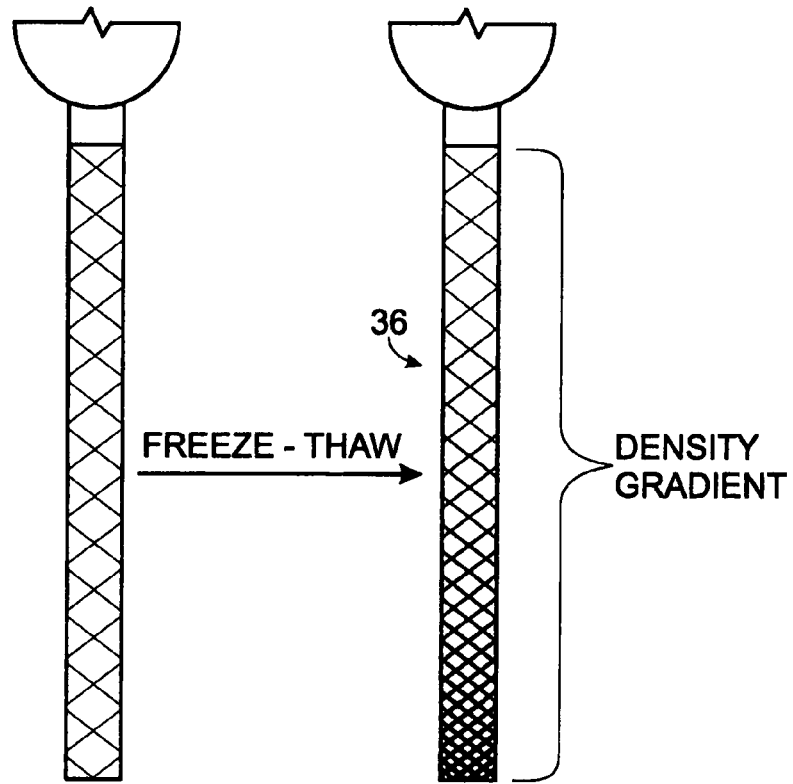
FIG. 6 is a schematic view of the establishment of a solution density gradient in an embodiment of a capillary channel by freezing and thawing the solution.

In this embodiment, the capillary channel 32 contains a single solution of appropriate density. By freezing and thawing the coupon 30 with the channel 32 in a substantially vertical orientation, the solution may establish a density gradient 36, as shown in FIG. 6.

A suitable density gradient may be established with any of a variety of suitable solutions, such as sucrose, for example. In one aspect of the method, solutions of iodinated contrast agents are used. In particular, the contrast agents IODIXANOL and/or IOHEXOL may be used to prepare the desired density gradient, as these agents are known to be effective in fractionating red blood cells. Additionally, these agents are water-soluble, chemically stable, biologically inert, of low viscosity, and exhibit low osmolarity.

The requisite freeze-thaw cycling may be performed as part of the manufacturing and supply process of the microfluidic coupons 10, 30, and/or it may be performed at the site of testing.

Figure 7:
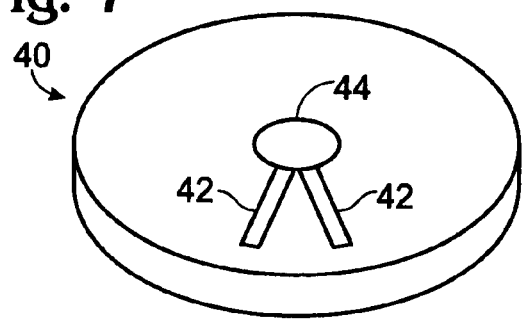
FIG. 7 is a schematic perspective view of yet another embodiment of a microfluidic coupon.
Figure 8:
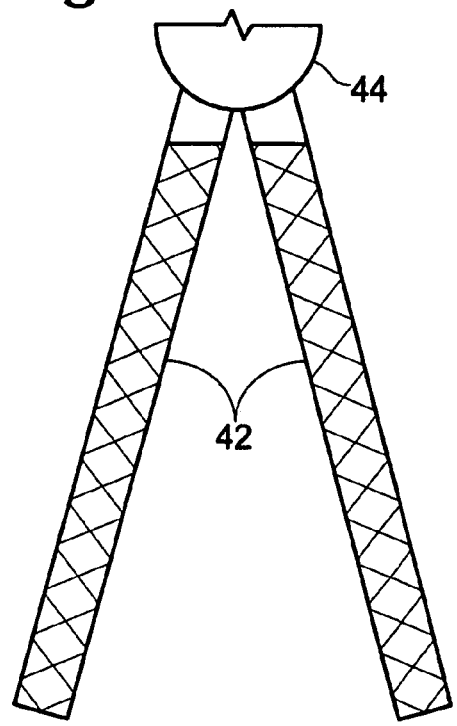
FIG. 8 is a schematic view of an embodiment of two capillary channels in a substantially vertical orientation.

Referring now to FIGS. 7 and 8 together, although the capillary channel 42 should remain substantially upright during the freeze-thaw cycles, the microfluidic coupon 40 may be engineered such that more than one capillary channel 42 on the coupon 40 may be utilized at one time. As shown in FIG. 7, a microfluidic coupon 40 is shown with two microfluidic channels 42 and one seal 44. The coupon 40 and the channels 42 should have a geometry and configuration so that a gradient may be established in each channel 42 when the coupon 40 is stored upright and on edge, as shown in FIG. 8. Typically, this entails the two or more channels 42 being separated by acute angles between them, where the angle is small enough such that gradients can be established in each channel 42. Multiple channels 42 might be used in order to provide testing redundancy, or to use different solution densities to interrogate different fractions of cells.

It should be appreciated that when loaded in a centrifuge, the coupon 10, 30, 40 may be unsymmetrically weighted. In such embodiments, the coupon 10, 30, 40 may either incorporate means to balance the coupon 10, 30, 40, or permit manual balancing, so that centrifugation may still be conducted without hazard.

Typically, upon establishing a density gradient in one or more channels, regardless of the method used to establish the gradient, the analysis of the sample of interest may be carried out in a similar fashion. Alternatively, however, the sample may be added to the capillary channel 12, 16, 32, 42, and the solution density gradient may be formed simultaneously with the fractionation of the sample components.

Figure 9:
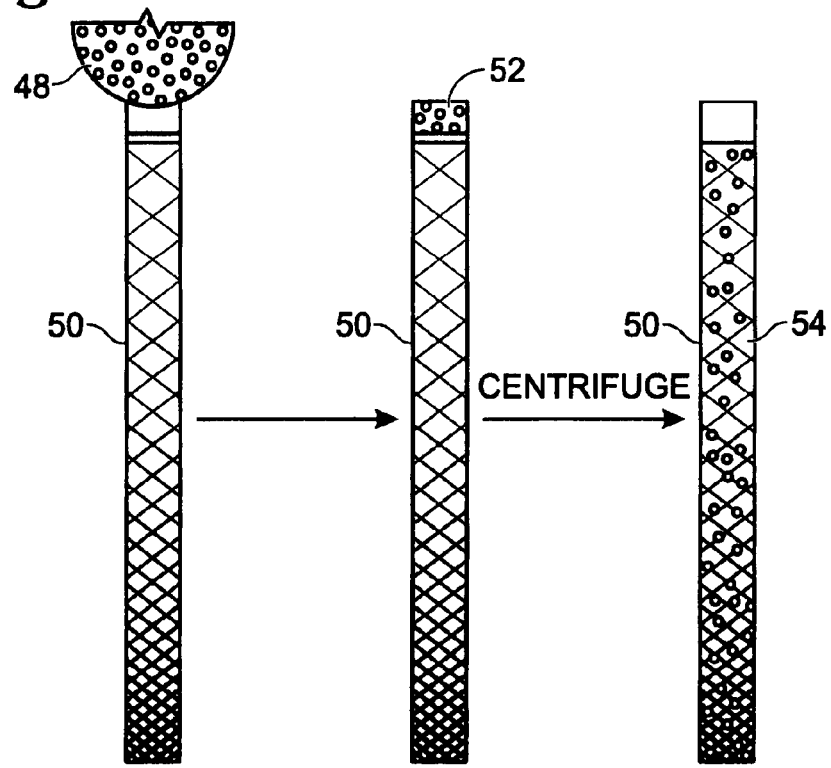
FIG. 9 is a schematic depiction of the addition of a sample to a solution density gradient, followed by centrifugation to separate the sample components.

Referring now to FIG. 9, after the gradient has been established, and seal 48 has been removed, the sample of interest 52 may be applied to the top of the capillary channel 50. Because the separation of the red blood cells is an equilibrium process, the blood cells may be applied at any point along the gradient. However, one end (e.g., the top) of the gradient is generally a convenient location to apply the sample. The application area may also include an overflow reservoir (not shown), in order to prevent the application of an excessive amount of the sample (e.g., blood and cells) to the gradient. After application of the sample, the gradient column is subjected to additional centrifugation, until the desired separation gradient 54 of the components of the sample is achieved.

Figure 10:
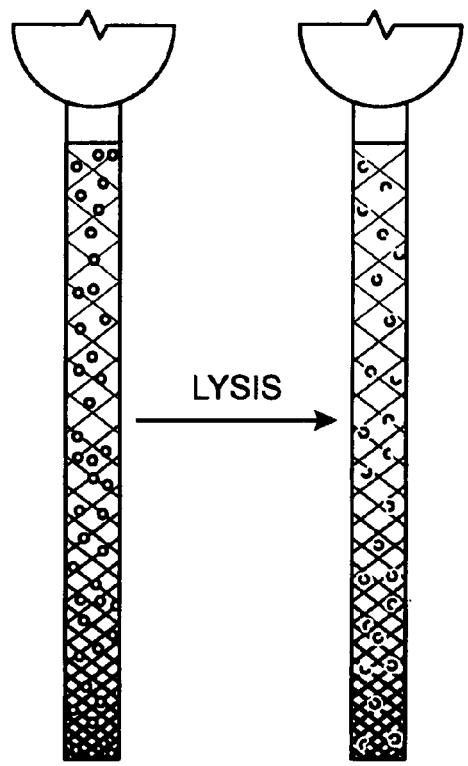
FIG. 10 is a schematic depiction of the lysis of separated sample components

After the density gradient of the sample components is achieved, the sample may be subjected to any of a variety of post-separation procedures. For example, the sample components may be lysed for further analysis. FIG. 10 depicts a cell lysis step after fractionation of the sample has been achieved. The lysis is depicted as occurring in the capillary channel 50 itself, which may be accomplished conveniently through the application of a strong electric field to the capillary channel 50. It is known that in the presence of an electric field cells may undergo electroporation, or complete lysis, depending on the strength and frequency of the applied electric field. Cell lysis may require a field gradient of about at least 100 KV/m, however this threshold may vary depending, at least in part, on the frequency of the signal and the medium in which the cells are suspended. A DC field may also be used for the lysis of the sample, but DC fields may lead to undesirable effects such as electrolysis and joule heating in the medium and cells. Furthermore, DC or low frequency fields may or may not be able to create a sufficient field gradient when the electrodes are insulated from the medium, as much of the voltage may be dropped across the insulating layer. It may therefore be advantageous to use an alternating field with a sufficiently high frequency to avoid these problems.

Close spacing of the electrodes used to apply the electric field may greatly reduce the required magnitude of the electrode source voltage. If the electrodes are built into the microfluidic coupon 10, 30, 40 itself, such that they are placed on opposite sides of the capillary channel 12, 16, 32, 42, 50, the resulting electrode spacing may be roughly the same as or slightly larger than the capillary channel width. As red blood cells typically have diameters of about 7 µm or 8 µm, the capillary channel may be as narrow as about 100 µm without creating a risk of clogging, particularly if an anticoagulant such as heparin or EDTA has been added to the solution. At an electrode spacing of 100 µm a source voltage of 20 Vrms would generate a field gradient of about 200 KV/m, neglecting the voltage drops that may result due to the presence of any intermediate insulating layers.

In addition, where analysis of the sample is performed via optical interrogation, the electrodes may be manufactured using an optically transparent material, such as indium-tin oxide (ITO).

The generation of a medium frequency (300 KHz to 3 MHz) signal for effectively lysing cells may be accomplished using analog oscillators (either discrete or integrated) or digital function generators, among other methods. The implementation of a simple oscillator circuit may be relatively cost effective. However, a digital circuit may offer enhanced flexibility. Additionally, depending on the oscillator architecture, an output buffer stage may be desirable in order to achieve the desired voltage levels.

Figure 11:
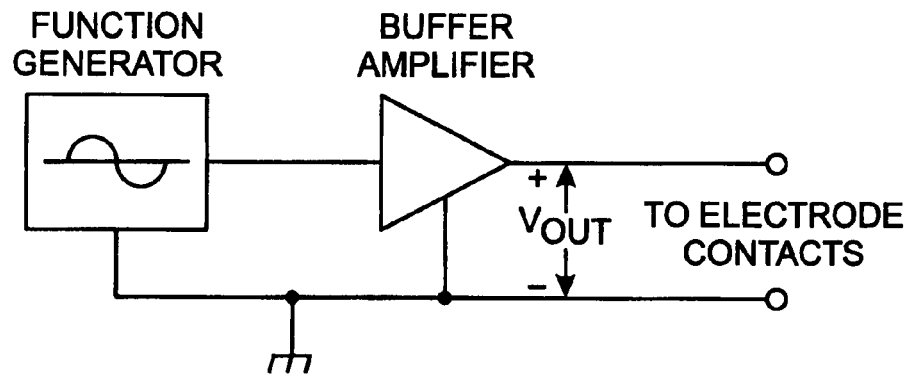
FIG. 11 is a circuit diagram for a simple circuit to generate an electric field for cell lysis.
Figure 12:
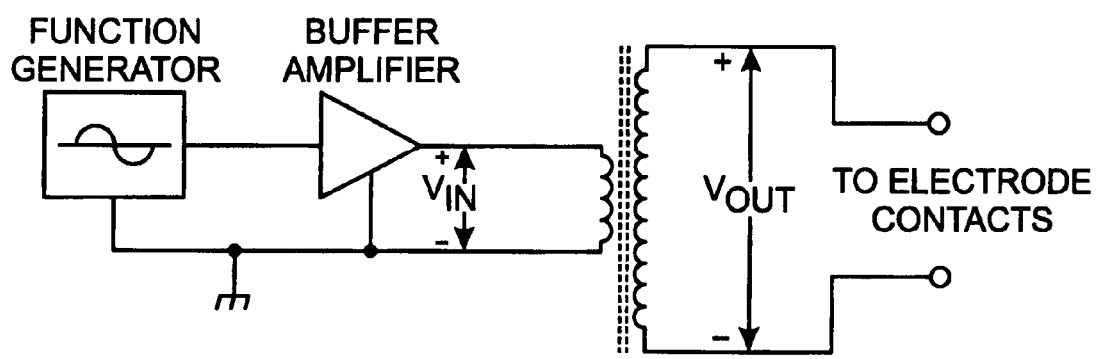
FIG. 12 is a circuit diagram for a circuit incorporating a transformer to generate an electric field for cell lysis.

A simple circuit similar to circuit 60 of FIG. 11 would be capable of generating 20 Vrms signals up to a few MHz using off the shelf integrated parts. If wider electrode spacing is required, significantly higher output voltages (e.g., up to 1000 Vrms) could be attained by adding a step-up transformer, as shown in the circuit 62 of FIG. 12. Discrete electronic solutions might also provide a wide range of output voltages, but these circuits may be more difficult to implement than integrated solutions. An intermediate option would be to use hybrid approaches, such as bootstrapped operational amplifier circuits which, while more complex than a fully integrated design, would be simpler to design and characterize than a discrete implementation. With careful component selection a hybrid circuit could be used to create output signals up to a few hundred volts with reasonable frequency response.

It may be desirable to insulate the electrodes from the medium to prevent unwanted chemical interactions. However, it is to be understood that some of the electric field is wasted across such an insulating boundary. An insulating barrier between the electrodes and the medium will appear as a series capacitance that is proportional to the dielectric constant of the barrier material and inversely proportional to the barrier thickness, and the signal voltage lost across this barrier will be inversely proportional to both the barrier capacitance and the signal frequency. The insulating barrier should therefore be as thin as possible to maximize the barrier capacitance, maximize the electric field present in the medium, and allow lower frequency signals to better penetrate the barrier. Such barriers include silicon nitride and silicon carbide. 30-40 nm silicon nitride insulating barriers have been fabricated and used in the embodiments disclosed herein.

Figure 13:
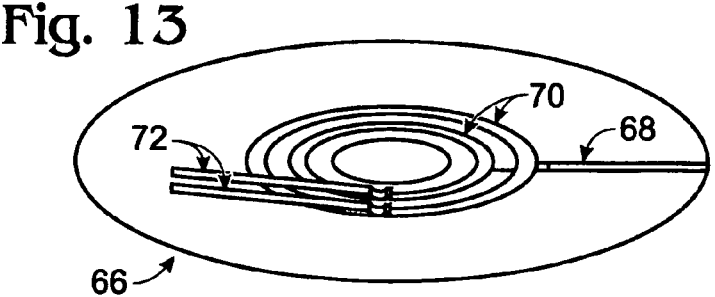
FIG. 13 is a schematic depiction of still another embodiment of a microfluidic coupon, where the coupon includes slip rings for the application of an electric signal to electrodes present on the coupon.

In one aspect of the disclosed method, it may be advantageous to apply a lysing electric field while the sample is being centrifuged. In order to deliver voltage to the electrodes present on the spinning microfluidic coupon 10, 30, 40, some type of slip ring and brush system may be used. For example, as depicted in FIG. 13, a microfluidic coupon 66 includes a capillary channel (not shown) and associated electrodes 68. Coupon 66 includes two slip rings 70 that are in electrical communication with the lysis electrodes 68, and are also in electrical communication with coupon brushes 72. Lysing voltage may be applied to the brushes 72 even as coupon 66 spins, resulting in an applied electric field at the capillary channel (not shown). With any slip ring system there may be sporadic loss of contact, so additional precautions such as large contact areas, conductive greases, etc. may also be used in conjunction with the disclosed slip ring system.

Figure 14:
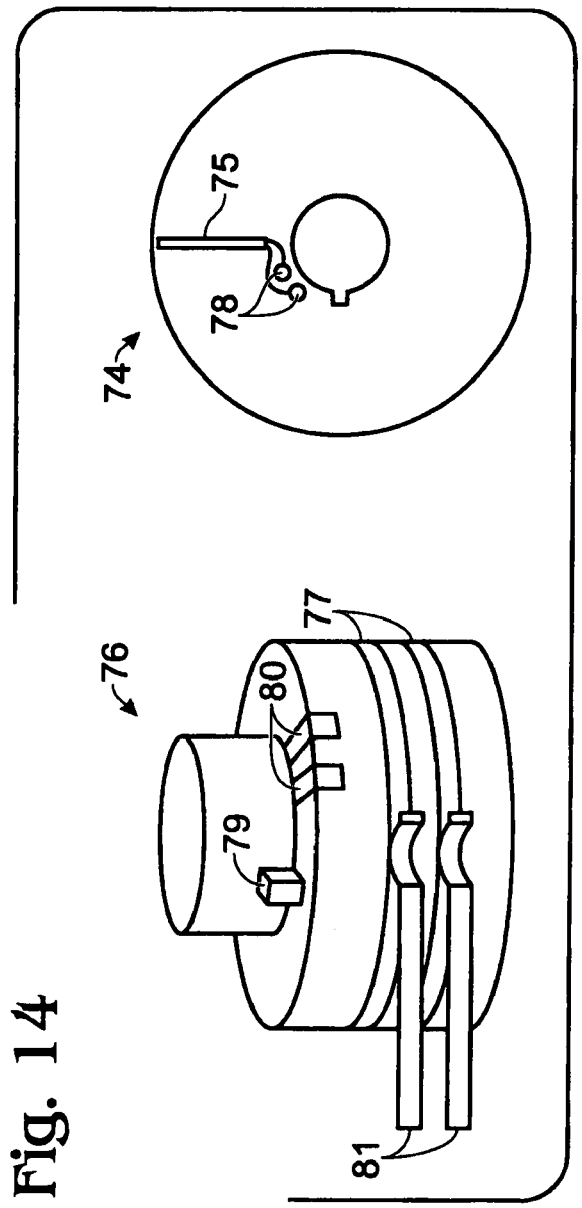
FIG. 14 is a schematic perspective view of an embodiment of a spindle and a schematic top view of an embodiment of a microfluidic coupon, where the spindle includes slip rings for the application of an electric signal to electrodes present on the coupon via the spindle.

Alternatively, as shown in FIG. 14, an electric field may be applied via slip rings 77 incorporated into a spindle 76 on which the microfluidic coupon 74 is spun. In FIG. 14, the microfluidic coupon 74 incorporating a capillary channel (not shown) and associated electrodes 75 is shown with a complementary spindle 76. Spindle 76 may be configured to incorporate a signal generating circuit inside spindle 76 such that DC power is passed through the slip rings 77. When spinning coupon 74 on spindle 76, the lysing signal could be passed to the coupon 74 through fixed contacts 78 on the underside of the coupon 74. The spindle 76 may incorporate one or more alignment features 79 to insure appropriate electrical contact between the coupon contacts 80 on the spindle 76 and the fixed contacts 78 on the underside of the coupon 74. The presence of sufficient bulk storage capacitors and supply filtering inside the spindle 76 may help eliminate the need to reduce noise resulting from spindle brushes 81. In another aspect of the disclosed spindle 76, concentric ring contacts (not shown) may be used in place of fixed coupon contacts 80, thereby eliminating the need for an alignment feature 79 to insure electrical contact.

Figure 15:
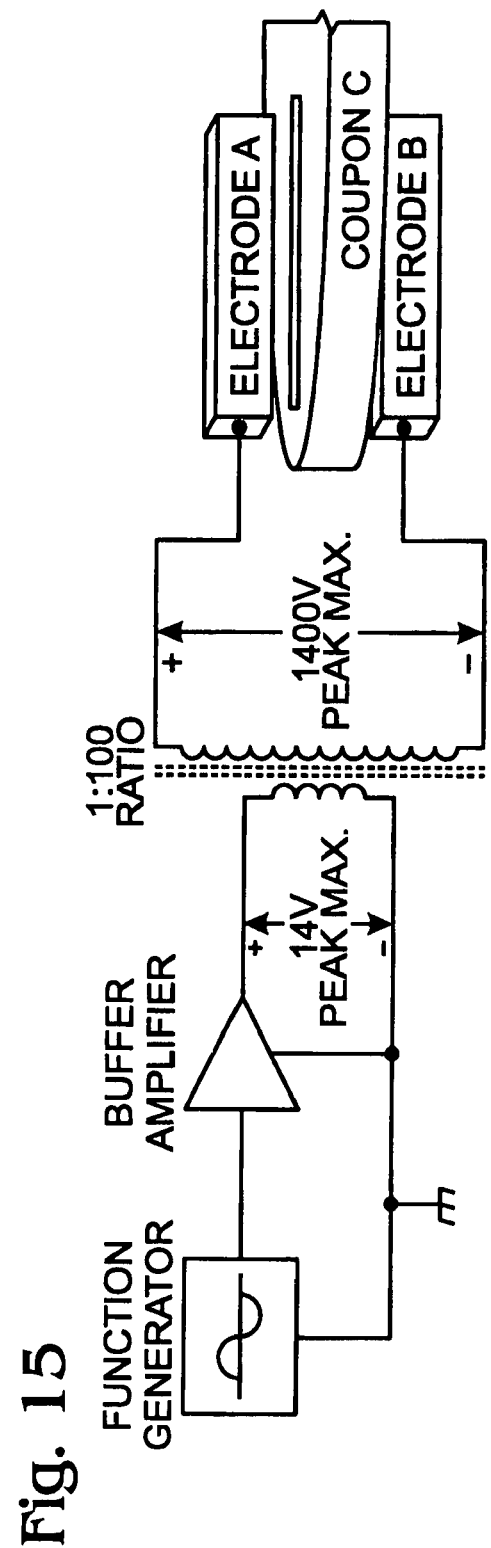
FIG. 15 is a schematic depiction of an embodiment of a system for application of an electric field to a microfluidic coupon by fixed electrodes floating above and below the coupon.

In yet another configuration, as shown in FIG. 15, an electric field may be applied using fixed electrodes A and B floating above and below the microfluidic coupon C, thereby generating an electric field perpendicular to the coupon C. However, the gap between the electrodes A and B and the medium may be large, requiring high voltages in order to generate sufficient field strength in the gradient medium.

Figure 16:
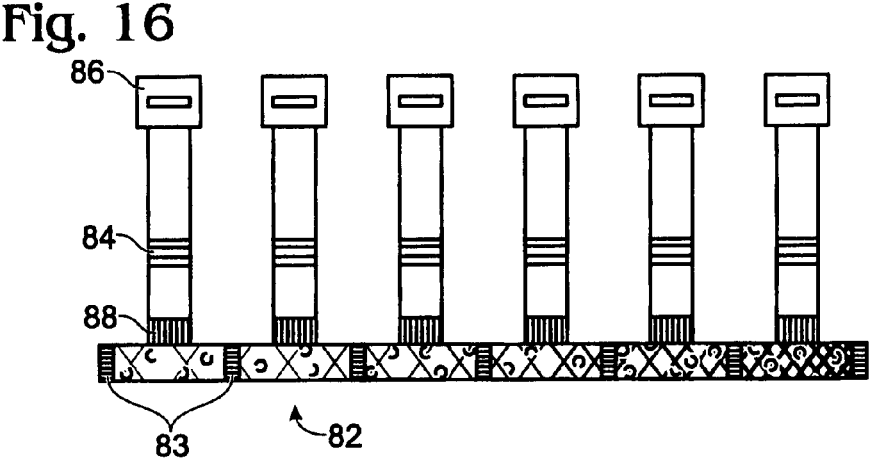
FIG. 16 is a schematic view of another embodiment of a system.

After the sample has been separated and lysed, the sample components may be detected by any method known in the art for lysed blood cell detection. For example, as shown in FIG. 16 a gradient capillary channel 82 containing gradient lysed blood cells, includes multiple resistors 83 along the gradient microchannel with associated detector regions 84 and vents 86 accessed through individual valves 88. A variety of active and passive valves may be used for this purpose, as discussed above and as is known in the art. Specifically, the use of a wax plug having a relatively low melting point can be used to create access to the detector regions 84 upon at least partial removal of the plug. In this embodiment, the resistors 83 can be heated to form gas bubbles which act to at least partially isolate the groups of lysed blood cells, and further provide a motive force to move the lysed blood cells through the valves 88 into the detector region 84 for subsequent $HbA_{1c}$ measurement.

Figure 17:
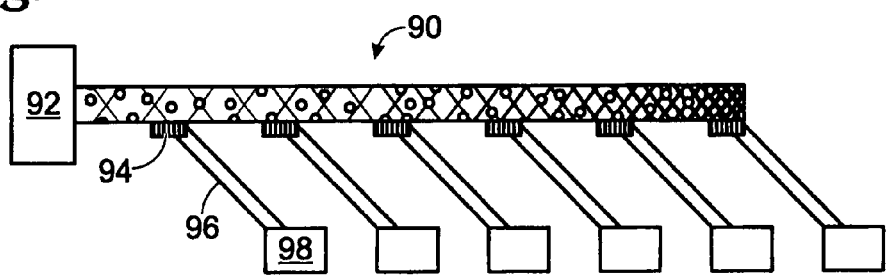
FIG. 17 is a schematic view of still another embodiment of a system.

In another aspect of the present disclosure, FIG. 17 depicts an alternative gradient capillary channel 90 containing a gradient of blood cells. The capillary channel 90 in this embodiment is connected to a particle detector 92. Once blood cells are detected as reaching the particle detector 92, individual valves 94 can be opened to receive the blood cells into a corresponding lysis microchannel 96, where the blood cells can be lysed by any number of methods as described above, and corresponding $HbA_{1c}$ measurements may be taken at the individual detector regions 98. The lysis microchannels 96 can be configured to receive the blood cells upon backflow of the cells, or by the use of resistors 83 as described with respect to FIG. 16. In this embodiment, each lysis microchannel 96 may be coupled to an analysis chamber (not shown), as described previously.

Figure 18:
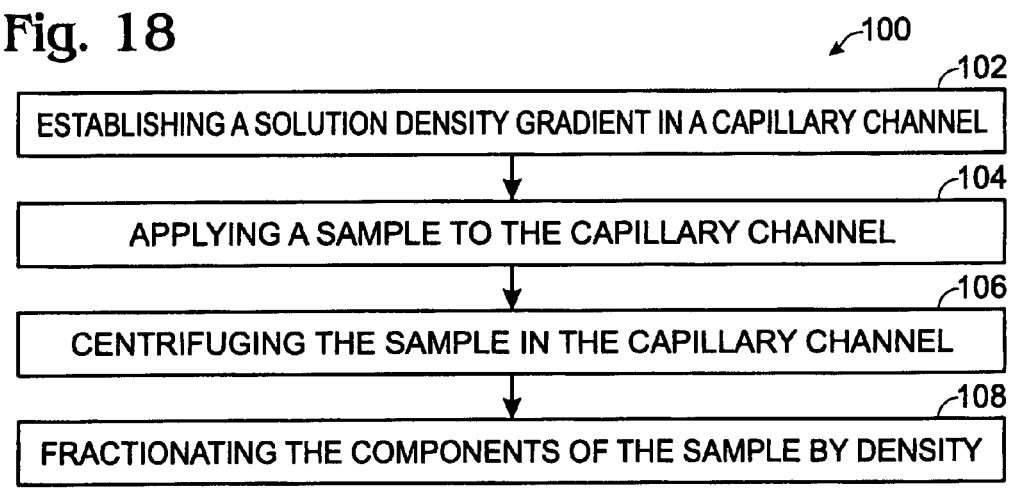
FIG. 18 is a flow diagram depicting an embodiment of a method of fractioning sample components.

Embodiments of the present microfluidic coupon 10, 30, 40, 66, 74 may be used in a method of fractionating sample components by their density, as shown in flowchart 100 of FIG. 18. The method may include establishing a solution density gradient in a capillary channel at 102, applying a sample to the capillary channel at 104, centrifuging the sample in the capillary channel at 106, and fractionating the components of the sample by density at 108. In one embodiment, the method lends itself to the measurement of glycated hemoglobin. In this embodiment, the sample may include red blood cells, and centrifuging the sample may establish a plurality of age-specific groups of red blood cells. The method may further include measuring an $HbA_{1c}$ level of at least one of the age-specific groups of red blood cells.

Although embodiments of the present invention have been shown and described with reference to the foregoing operational principles, it will be apparent to those skilled in the art that various changes in form and detail can be made without departing from the spirit and scope of the invention as defined in the following claims. Various configurations of apertures, lugs, and cleat bodies may be envisioned, as well as a variety of possible interactions between the packaging tie and the apertures and lugs of the cleat. The present invention is intended to embrace all such alternatives, modifications and variances, including all novel and non-obvious combinations and subcombinations of the various elements, features, functions and/or properties disclosed herein.

What is claimed is:

1. A method of fractioning components of a sample by sequentially:
   a) establishing a solution density gradient in a capillary channel wherein the solution density gradient is established by combining at least two distinct solutions in the capillary channel and centrifuging the combined solutions;
   b) applying the sample to the capillary channel: and
   c) centrifuging the sample in the capillary channel, thereby separating the components of the sample by density.

2. The method of claim 1, wherein the sample includes red blood cells.

3. The method of claim 2, wherein the red blood cells are from whole blood.

4. The method of claim 1, wherein the two distinct solutions are separated by a barrier in the capillary channel.

5. The method of claim 4, wherein the barrier is a paraffin plug and combining the solutions includes removing the plug by heating the paraffin.

6. The method of claim 4, wherein the barrier is a hydrophobic region of the capillary channel, and combining the solutions includes centrifuging the capillary channel.

7. The method of claim 1, wherein the solution density gradient is established by at least one freeze-thaw cycle of the solution in the capillary channel.

8. The method of claim 1, wherein the sample includes red blood cells, and fractioning the components of the sample includes establishing a plurality of age-specific groups of red blood cells in the solution density gradient.

9. The method of claim 8, further comprising measuring an HbA 1 c level of at least one of the age-specific groups of red blood cells.

10. The method of claim 9, wherein measuring the HbA1c level of at least one of the age-specific groups of red blood cells includes lysing the red blood cells.

11. The method of claim 10, wherein lysing the red blood cells includes applying an electric field to the red blood cells.

12. A method for measuring glycated hemoglobin comprising: providing a microfluidic coupon that is configured to be spun in a centrifuge, the said coupon comprising at least one capillary channel that encloses a density gradient solution and a sample well in connection with said capillary channel; providing a centrifuge, first spinning the microfluidic coupon in the centrifuge to form a solution density gradient in the at least one capillary channel, adding the sample to said sample well, providing a centrifuge, and second spinning of the microfluidic coupon to separate the red blood cells into age-specific groups and measuring the glycated hemoglobin levels of at least one group of the age-specific groups.

13. The method of claim 12, wherein the sample comprises a whole blood sample.

14. The method of claim 12, further comprising a lysing mechanism configured to cause lysis of the red blood cells.

15. The method of claim 14, wherein the lysing mechanism includes electrodes adjacent to the at least one capillary channel and the lysing mechanism is adapted to apply an electric field to the at least one capillary channel.

16. The method of claim 12, wherein the method is a part of a single, integrated device.

* * * * *

UNITED STATES PATENT AND TRADEMARK OFFICE
CERTIFICATE OF CORRECTION

PATENT NO.        : 7,534,618 B2                                          Page 1 of 1
APPLICATION NO.   : 11/881531
DATED             : May 19, 2009
INVENTOR(S)       : Tyvoll et al.

It is certified that error appears in the above-identified patent and that said Letters Patent is hereby corrected as shown below:

In column 5, line 6, delete "Theological" and insert -- rheological --, therefor.

In column 12, line 13, after "channel" delete ":" and insert -- ; --, therefor.

In column 12, line 36, delete "HbA 1 c" and insert -- $HbA_{1c}$ --, therefor.

In column 12, line 38, delete "HbA1c" and insert -- $HbA_{1c}$ --, therefor.

In column 12, line 53, delete "glycatcd" and insert -- glycated --, therefor.

Signed and Sealed this

Seventeenth Day of November, 2009

David J. Kappos
*Director of the United States Patent and Trademark Office*